United States Patent
Mullens et al.

(10) Patent No.: US 6,467,642 B2
(45) Date of Patent: Oct. 22, 2002

(54) CRYOGENIC SHIPPING CONTAINER

(76) Inventors: Patrick L. Mullens, 2124 Santiago St., Covina, CA (US) 91724; Gregg Emmel, 1120 Princeton Dr., Marina Del Rey, CA (US) 90292; Kevin Giesy, 14999 Camden Ave., Chino Hills, CA (US) 91709; Christy Thomas, 1120 Princeton Dr., Marina Del Rey, CA (US) 90292

(*) Notice: Subject to any disclaimer, the term of this patent is extended or adjusted under 35 U.S.C. 154(b) by 4 days.

(21) Appl. No.: 09/753,194

(22) Filed: Dec. 29, 2000

(65) Prior Publication Data
US 2002/0084277 A1 Jul. 4, 2002

(51) Int. Cl.7 .............................. F17C 1/00; F17C 13/00
(52) U.S. Cl. .............................. 220/560.1; 220/560.12; 220/367.1; 220/560.07
(58) Field of Search .................. 220/560.24, 560.07, 220/560.1, 560.12, 560.4, 367.1

(56) References Cited

U.S. PATENT DOCUMENTS

| | | |
|---|---|---|
| 2,001,989 A | 5/1935 | Theuerkauf |
| 2,215,989 A | 9/1940 | Wolf |
| 2,396,459 A | 3/1946 | Dana |
| 2,986,891 A | 6/1961 | McMahon |
| 3,007,596 A | 11/1961 | Matsch |
| 3,108,840 A | 10/1963 | Conrad et al. |
| 3,168,362 A | 2/1965 | Perkins |
| 3,187,937 A | 6/1965 | Berta |
| 3,204,849 A | 9/1965 | Vinney |
| 3,238,002 A | 3/1966 | O'Connell et al. |
| 3,298,185 A | 1/1967 | Loudon |
| 3,375,933 A | 4/1968 | Rodman |
| 3,507,444 A | 4/1970 | Werby |
| 3,602,003 A | 8/1971 | Hampton |
| 3,625,351 A | 12/1971 | Eisenberg |
| 3,651,926 A | 3/1972 | Elfast, Jr. |
| 3,670,918 A | 6/1972 | Mitchell |
| 3,675,844 A | 7/1972 | Sorrell |

(List continued on next page.)

FOREIGN PATENT DOCUMENTS

| | | |
|---|---|---|
| CA | 1219821 | 3/1987 |

*Primary Examiner*—Joseph M. Coy
(74) *Attorney, Agent, or Firm*—Ray L. Anderson

(57) ABSTRACT

A shipping container with an outer shipping container shell and a support assembly for holding a dewar vessel within the outer shipping container shell and providing impact and vibration resistance to the dewar vessel. The dewar vessel has an inner vessel that holds a specimen chamber and plastic foam between its inner wall and the specimen chamber. The specimen chamber allows liquid cryogen to pass through it into the plastic foam, allows liquid cryogen in a vapor phase liquid state to pass from the plastic foam into it, and acts as a filter to prevent particles or fragments of the plastic foam from entering into it. The specimen chamber is an open-celled porous thermoplastic material that is cryogenically compatible such as an aerated polypropylene foam. The plastic foam is an open cell plastic foam such as a phenolic foam. The plastic foam can hold a normal charge of liquid cryogen in a dry vapor state regardless of the container's spatial orientation. The plastic foam can be made of multiple foam segments separated by a capillarity separation layer. A self-venting cap is used to restrict access to the specimen chamber when it forms a compression seal with an inner circumference of the neck of the dewar vessel. The shipping container is configured so that a reservoir will be formed within the dewar vessel when the container rests on its side so that gravity will not force vapor phase liquid cryogen in the reservoir out of the dewar vessel. The shipping container complies with Department of Transportation/International Air Transport Association (DOT/IATA) Dangerous Goods Regulations.

79 Claims, 8 Drawing Sheets

U.S. PATENT DOCUMENTS

| | | |
|---|---|---|
| 3,698,200 A | 10/1972 | Johnson et al. |
| 3,705,498 A | 12/1972 | Dehaan |
| 3,717,005 A | 2/1973 | McGrew et al. |
| 3,819,106 A | 6/1974 | Schuster |
| 3,828,608 A * | 8/1974 | Yamamoto ............. 220/560.12 |
| 3,875,754 A | 4/1975 | Faust et al. |
| 3,938,346 A | 2/1976 | Ovchinnikov et al. |
| 3,948,409 A | 4/1976 | Ochinnikov et al. |
| 3,948,459 A * | 4/1976 | Ovchinnikov et al. . 220/560.12 |
| 3,984,222 A | 10/1976 | Dehaan |
| 3,999,653 A | 12/1976 | Haigh et al. |
| 4,000,815 A | 1/1977 | Wingbro et al. |
| 4,131,200 A | 12/1978 | Rainfret |
| 4,168,014 A * | 9/1979 | Schultz et al. ......... 220/560.12 |
| 4,240,547 A | 12/1980 | Taylor |
| 4,259,846 A | 4/1981 | Rudolphi |
| 4,264,031 A | 4/1981 | Goebel |
| 4,306,425 A | 12/1981 | Sitte et al. |
| 4,377,077 A | 3/1983 | Granlund |
| 4,390,111 A | 6/1983 | Robbins et al. |
| 4,396,113 A | 8/1983 | Gail et al. |
| 4,411,138 A | 10/1983 | Leithauser et al. |
| 4,455,842 A | 6/1984 | Granlund |
| 4,481,779 A | 11/1984 | Barthel |
| 4,495,775 A | 1/1985 | Young et al. |
| 4,510,621 A | 4/1985 | Sak et al. |
| 4,646,934 A | 3/1987 | McAllister |
| 4,670,396 A | 6/1987 | Bear et al. |
| 4,694,655 A | 9/1987 | Seidel et al. |
| 4,729,494 A | 3/1988 | Peillon et al. |
| 4,741,346 A | 5/1988 | Wong et al. |
| 4,790,141 A | 12/1988 | Glascock |
| 4,821,907 A | 4/1989 | Castles et al. |
| 4,872,563 A | 10/1989 | Warder et al. |
| 4,903,493 A | 2/1990 | Van Iperen et al. |
| 4,925,060 A | 5/1990 | Gustafson |
| 4,932,533 A | 6/1990 | Collier |
| 4,948,035 A | 8/1990 | Wischoff |
| 4,974,423 A | 12/1990 | Pring |
| 4,988,014 A * | 1/1991 | Varuchese et al. ..... 220/560.12 |
| 5,005,362 A | 4/1991 | Weltmer, Jr. et al. |
| 5,024,865 A | 6/1991 | Insley |
| 5,029,699 A | 7/1991 | Insley et al. |
| 5,040,678 A | 8/1991 | Lenmark, Sr. et al. |
| 5,160,021 A | 11/1992 | Sibley et al. |
| 5,199,795 A | 4/1993 | Russo et al. |
| 5,219,504 A | 6/1993 | Insley |
| 5,291,997 A | 3/1994 | He et al. |
| 5,296,834 A | 3/1994 | Urban |
| 5,321,955 A | 6/1994 | Leonard |
| 5,355,684 A | 10/1994 | Guice |
| 5,419,143 A | 5/1995 | Leonard et al. |
| 5,462,875 A | 10/1995 | Barr et al. |
| 5,464,116 A | 11/1995 | Aoki et al. |
| 5,484,100 A | 1/1996 | Rigby |
| 5,509,255 A | 4/1996 | Rutledge |
| 5,578,491 A | 11/1996 | Kayal et al. |
| 5,582,887 A | 12/1996 | Etheredge |
| 5,620,110 A | 4/1997 | Delatte et al. |
| 5,651,473 A * | 7/1997 | Preston e al. .......... 220/560.12 |
| 5,711,446 A | 1/1998 | Jeffs et al. |
| 5,779,089 A | 7/1998 | West |
| 5,829,594 A | 11/1998 | Warder |
| 5,833,057 A | 11/1998 | Char et al. |
| 5,856,172 A | 1/1999 | Greenwood et al. |
| 5,894,733 A | 4/1999 | Brodner |
| 5,906,101 A | 5/1999 | Rajotte et al. |
| 5,921,396 A | 7/1999 | Brown, Jr. |
| 5,928,935 A | 7/1999 | Reuss, Jr. et al. |
| 5,934,099 A | 8/1999 | Cook et al. |
| 5,935,848 A | 8/1999 | Sputtek et al. |
| 5,947,960 A | 9/1999 | Griswold |
| 6,036,045 A | 3/2000 | West |
| 6,119,465 A | 9/2000 | Mullens et al. |
| 6,145,688 A | 11/2000 | Smith |
| 6,146,875 A | 11/2000 | Ward |

* cited by examiner

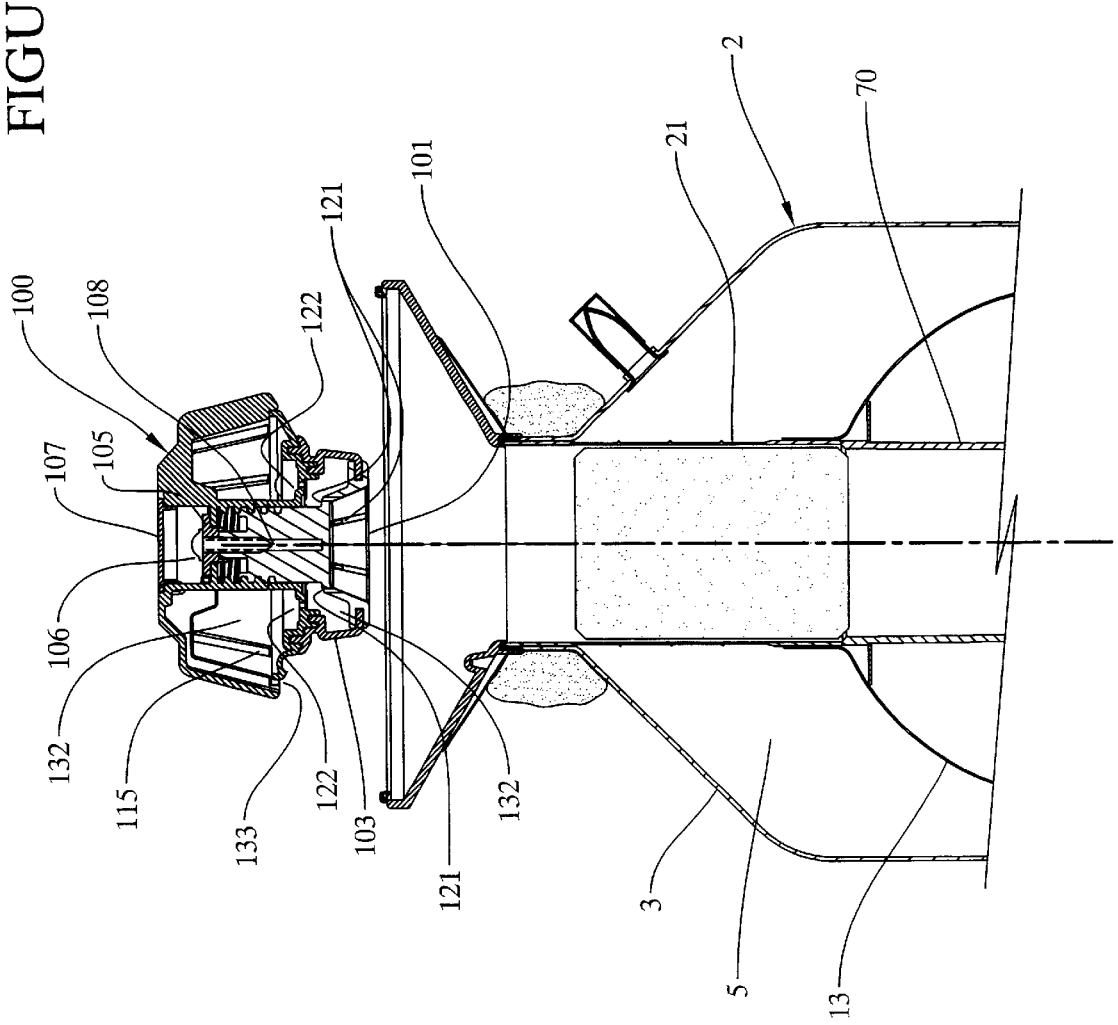

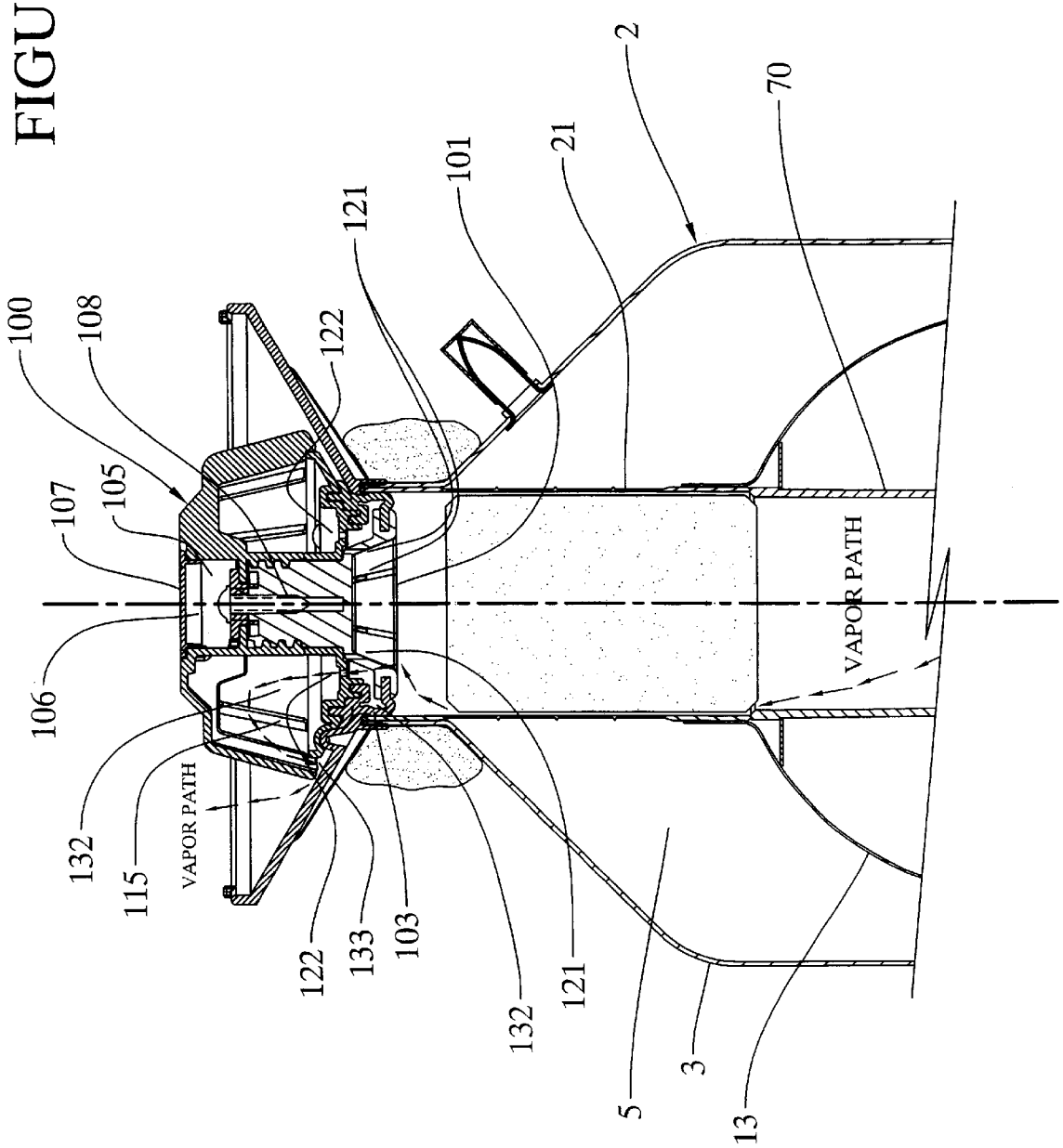

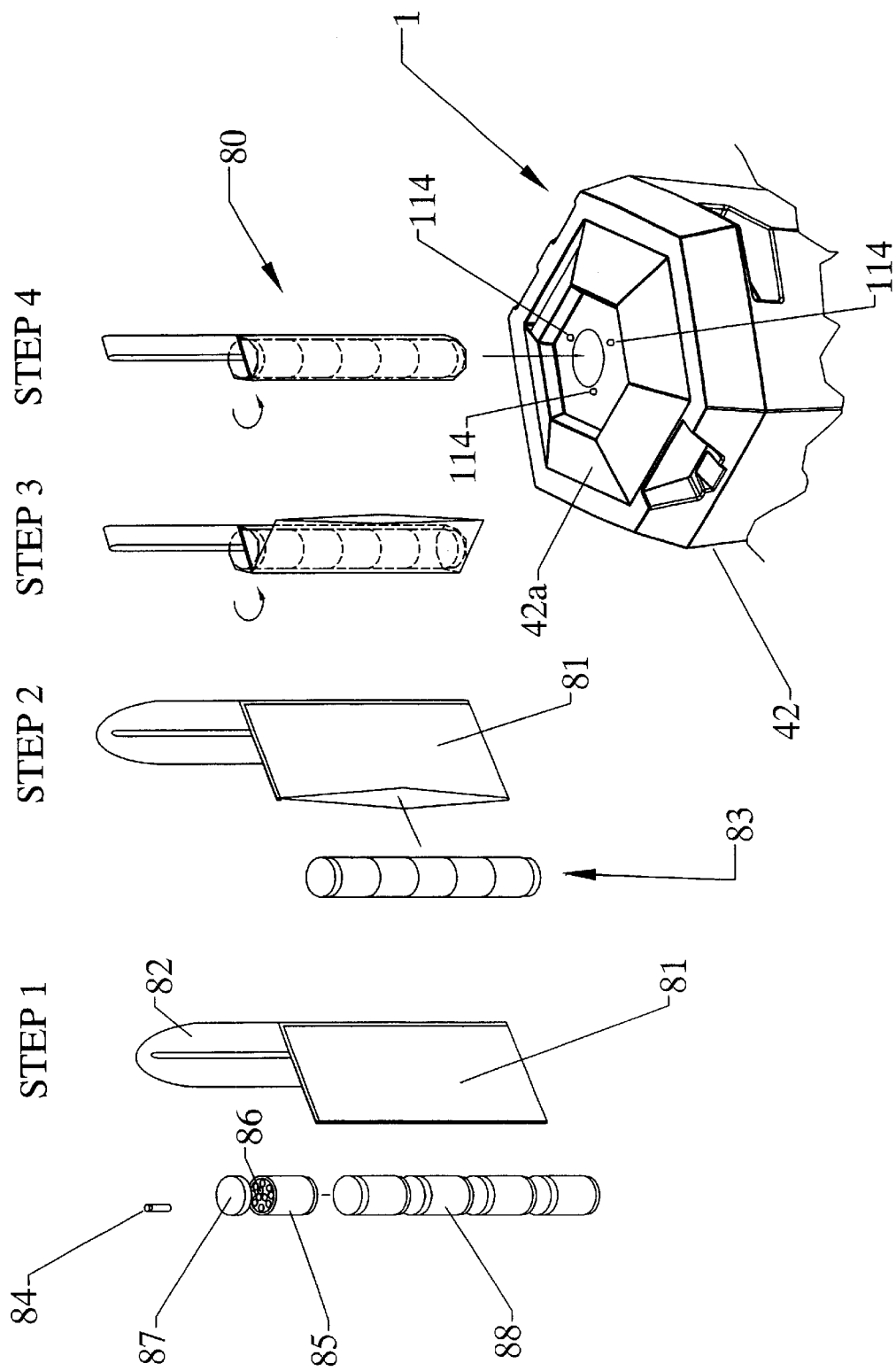

CRYOGENIC SHIPPING CONTAINER

CROSS REFERENCE TO RELATED APPLICATIONS

The present application is related to the following three patent applications, all of which are specifically incorporated herein by reference, and all of which are being filed concurrently with the present application on the same date: Ser. No. 09/753,195, entitled "SELF-VENTING CAP FOR A NECK OF A DEWAR VESSEL," Ser. No. 09/753,208, entitled "SPECIMEN CHAMBER FOR A CRYOGENIC SHIPPING CONTAINER," and Ser. No. 09/753,207, entitled "CONTAINMENT SYSTEM FOR SAMPLES OF DANGEROUS GOODS STORED AT CRYOGENIC TEMPERATURES."

FIELD OF THE INVENTION

The present invention is in the field of cryogenic shipping containers.

BACKGROUND OF THE INVENTION

To ensure reproducible results in research and biotechnical processes, today's scientists and clinical practitioners have found it necessary to genetically stabilize living cells and preserve the integrity of complex molecules for storage and transport. This is accomplished by containing these materials in enclosures where cryogenic temperatures are continuously maintained at or near liquid nitrogen or vapor phase liquid nitrogen temperatures (77K and 100K, respectively).

Advances in cryopreservation technology have led to methods that allow low-temperature maintenance of a variety of cell types and molecules. Techniques are available for the cryopreservation of cultures of viruses and bacteria, isolated tissue cells in tissue culture, small multi-cellular organisms, enzymes, human and animal DNA, pharmaceuticals including vaccines, diagnostic chemical substrates, and more complex organisms such as embryos, unfertilized oocytes, and spermatozoa. These biological products must be transported or shipped in a frozen state at cryogenic temperatures to maintain viability. This requires a shipping enclosure that can maintain a cryogenic environment for up to 10 days and meet other shipping requirements such as being relatively impervious to mechanical shock and effects of directional orientation.

In addition to the already existing difficulties posed in shipping heat-sensitive biologicals, the International Air Transport Association (IATA) imposed new regulations which became effective in January 1995 pertaining to all shipments that include specimens containing infectious agents or potentially infectious agents. These regulations, endorsed by the US Department of Transportation (DOT) and applicable to all public and private air, sea, and ground carriers, imposed greatly increased requirements upon shipping units to survive extensive physical damage (drop-testing, impalement tests, pressure containment tests, vibration tests, thermal shock, and water damage) without leakage and without fracture of the internal, primary receptacles (vials). Implementation of this regulation further complicated the shipping of frozen biologicals.

Even though bioshippers are currently available using liquid nitrogen as a refrigerant, little innovation has taken place in the design of packaging for low-temperature transport. Current shippers are generally vulnerable to the physical damage and changes in orientation encountered during routine shipping procedures. Additionally, these shippers rarely comply with the IATA Dangerous Goods Regulation (effective January 1995 or as later amended). Commercial vendors have not developed or certified a cost-effective, standardized shipping unit with the necessary specimen capacity and hold time to meet user demands.

One of the main criticisms of current shippers is price, which varies from $500.00 to $1,000.00 or more per unit. This substantially limits their use for the transport of many biologicals. Because of the initial cost and limited production of these containers, they are designed to be reusable. However, the cost of return shipping of these heavy containers is significant, particularly in international markets.

Users also complain about the absorbent filler used in the current dry shippers, which breaks down with continuous use, contaminating the interior of the container. In fact, one large user of these containers has essentially centered their entire shipping operation around cleaning the broken down absorbent material from the inside of these containers after each use.

Another problem cited by users of currently available dry shippers relates to the functional hold time versus static hold time. Static hold time pertains to a fully charged shipper with no heat load, sitting upright, e.g., essentially not in use. Functional hold time refers to the fully charged shipper in use and containing samples, e.g., in the process of being handled and transported. Even though the static hold time is often promoted as being 20 days, if the container is tilted or positioned on its side, the hold time diminishes to hours as opposed to days. This occurs because the liquid nitrogen transitions to the gaseous (vapor) phase more rapidly resulting in outgassing. The liquid nitrogen can also simply leak out of the container when it is positioned on its side.

The current cryogenic containers are promoted as being durable because they are of metal construction. However, rugged handling frequently results in the puncturing of the outer shell or cracking at the neck, resulting in loss of the high vacuum insulation. This renders them useless. The metal construction also adds to the weight of the container, thereby adding substantially to shipping costs.

Thus, there is a need for an improved cryogenic container that can be used to ship biologicals safely, reliably, and economically.

U.S. Pat. No. 6,119,465 seeks to meet this need by using unique, lightweight, low-cost, durable composites and polymers in a semi-disposable vapor phase liquid nitrogen bioshipper. This is accomplished in an inherently simple, reliable, and inexpensive device that will result in reduced shipping costs, enhanced reliability and safety, and fewer service requirements.

The present invention builds upon the framework laid by U.S. Pat. No. 6,119,465, the disclosure of which is specifically incorporated herein by reference. This is done by use of a cryogenic shipping container that has many significant advances over what is disclosed in our earlier patent. The end result is a much improved cryogenic shipping container that is more economical while still being reliable.

SUMMARY OF THE INVENTION

The present invention is generally directed to a portable, insulated shipping container. The shipping container has an outer shipping container shell and a support assembly for holding a dewar vessel within the outer shipping container shell and providing impact and vibration resistance to the dewar vessel. The dewar vessel has an inner vessel that holds a specimen chamber and plastic foam between its inner wall and the specimen chamber. The specimen chamber allows liquid cryogen to pass through it into the plastic foam, allows liquid cryogen in a vapor phase liquid state to pass from the plastic foam into it, and acts as a filter to prevent particles or fragments of the plastic foam from entering into it. It is preferred that the specimen chamber is an open-celled porous thermoplastic material that is cryogenically compatible, and it is especially preferred that it be an aerated polypropylene foam. It is preferred that the plastic foam is an open cell plastic foam, and it is especially preferred that it be a phenolic foam.

In a first, separate group of aspects of the present invention, the plastic foam can hold a normal charge of liquid cryogen in a dry vapor state regardless of the container's spatial orientation. The plastic foam can be made of multiple foam segments having a maximum thickness less than a critical height with each segment being separated by a capillarity separation layer. The thickness of the foam segments is preferably selected so that the head pressure of the plurality of foam segments will not cause liquid cryogen to ooze or flow out of the foam segments when their spatial orientation is changed. This thickness can be less than approximately four inches. The foam can occupy substantially all of the volume between the inner wall of the inner vessel and the sample chamber. Materials suitable for use as the capillarity separation layer include paper products treated to resist water and spunbonded olefin film.

In other, separate aspects of the present invention, a self-venting cap is used to restrict access to the specimen chamber when it forms a compression seal with an inner circumference of the neck of the dewar vessel. The cap creates one or more tortuous paths through it when it is in the compression seal position. The cap can be made of a lower component with a first plurality of apertures, an upper component having a second plurality of apertures, a seal held between the lower and upper components, and a third component secured to the upper component. It is especially desirable that the components of the cap in the vapor paths are made of a cryogenically compatible material that is non-metallic and non-conductive. A first chamber can be formed between the lower and upper components while a second chamber and a vent opening can be formed between the upper and third components. Vapor can travel through the cap in any of multiple tortuous vapor paths beginning with the first plurality of apertures and then proceeding through the first chamber, the second plurality of apertures, the second chamber and then out a vent opening. One or more semi-permeable membranes can be used to prevent moisture (water vapor) from entering into the dewar vessel while still allowing vaporous cryogen to exit from the dewar vessel.

In still other, separate aspects of the present invention, the shipping container is configured so that a reservoir will be formed within the dewar vessel when the container rests on its side so that gravity will not force vapor phase liquid cryogen in the reservoir out of the dewar vessel. The reservoir can be formed by configuring the container so that there will be an angle of approximately six degrees or greater between a flat planar surface and a cross section of the specimen chamber taken from an upper end closest to its top wall and extending down through a lower end closest to its base when the side wall of the container is resting on the flat planar surface. The reservoir can also be formed by a plane that is substantially parallel to the flat planar surface which intersects with the base of the specimen chamber and a first aperture of a self-venting cap that forms a compression seal with the neck of the dewar vessel.

In yet still other, separate aspects of the present invention, the shipping container can have a funnel-shaped vessel plate affixed to the dewar vessel. The shipping container can be made of a rigid thermoplastic material having a base, a side wall and a top wall. The top wall can be connected to the side wall by a movable access assembly, such as a hinge and latching mechanism, and the latching mechanism can be held in a locked position by a lock. The side wall can include a top side wall with a pocket for holding paperwork and a top opening for accessing a dewar opening in the dewar vessel and the top side wall can be covered by the top wall. A safety strap with a locking mechanism, such as an adjustable buckle, can be affixed to the bottom of the dewar vessel and surround the dewar vessel in a closed position so that it also holds the self-venting cap in place. An inner plug of a cryogenically compatible insulating plastic foam with a handle can be held in the neck portion between the self-venting cap and the specimen container. The support assembly can have multiple parts or be a single piece, such as a material that is injected or poured into the shipping container's shell to fill the available space.

In a further, separate aspect of the present invention, the portable shipping container can be made to comply with Department of Transportation/International Air Transport Association (DOT/IATA) Dangerous Goods Regulations.

Accordingly, it is a primary object of the present invention to provide an improved, portable, insulated shipping container that uses a dewar vessel that can be charged with a liquid cryogen.

This and further objects and advantages will be apparent to those skilled in the art in connection with the drawings and the detailed description of the preferred embodiment set forth below.

BRIEF DESCRIPTION OF THE DRAWINGS

FIGS. 5A–5C are a planar cross section of a preferred embodiment of a portable, insulated shipping container showing connection of a preferred self-venting cap.

FIG. 6 depicts an assembly of a preferred embodiment of a containment system.

DETAILED DESCRIPTION OF THE PREFERRED EMBODIMENTS

Figure 1:
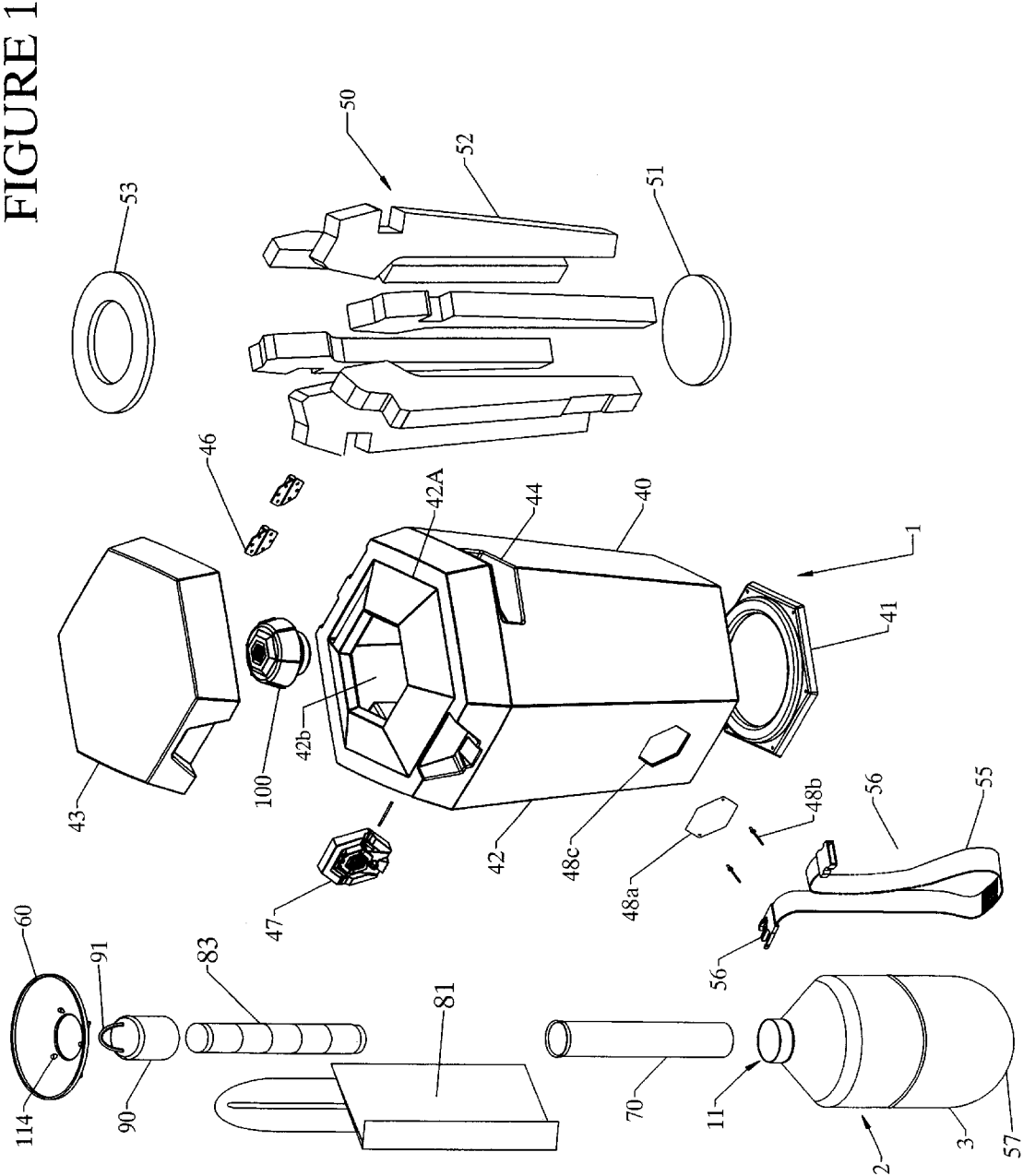
FIG. 1 is an exploded assembly drawing of a preferred embodiment of a portable, insulated shipping container according to the present invention with a containment system for dangerous materials.

The preferred embodiments of the present invention can be used as part of an overall system that utilizes several inventions. Broadly speaking, there is an overall cryogenic shipping container system. Within the shipping container, there is a dewar vessel. Within the dewar vessel, there is a specimen chamber for holding specimens. And, in certain applications, such as shipping of dangerous goods, the specimens are held within a containment system. Although FIGS. 1–6 are described in greater detail below, the following is a glossary of the elements identified in the Figures:

1 portable, insulated shipping container
2 dewar vessel
3 outer casing of dewar vessel 2
3a upper half of outer casing 3
3b bottom half of outer casing 3
4 opening at top of outer casing 3
5 evacuable space between outer casing 3 and inner casing 13
6 getter pack
7 desiccant
8 nipple
9 layer of super insulation
10 dewar opening into inner vessel 13
11 inner vessel of dewar vessel 2
13 upper half of inner vessel 13
13a lower half of inner vessel 13
13b opening at top of inner vessel 13
15 inner wall of inner vessel 13
21 neck portion of dewar vessel 2
30 plastic foam
31 foam segment of plastic foam 30
32 capillarity separation layer of foam 30
40 outer shipping container shell
41 base of outer shipping container shell 40
42 side wall of outer shipping container shell 40
42a a top side wall of side wall 42
42b a top opening formed in top side wall 42a
43 top wall of outer shipping container shell 40
44 handle molded in outer shipping container shell 40
45 pocket for paperwork formed in outer shipping container shell 40
46 hinge mechanism
47 latch mechanism
48 certification plate assembly
48a certification plate
48b rivet for certification plate assembly 48
48c indentation in outer shipping container shell 40 for certification plate
50 support assembly for dewar vessel 2
51 bottom portion of support assembly 50
52 side rib portion of support assembly 50
53 top portion of support assembly 50
55 safety strap
56 adjustable buckle of safety strap 55
57 outer bottom of dewar vessel 2
60 funnel-shaped vessel plate
61 support for plate 60
62 spray foam
70 specimen chamber
71 side wall of specimen chamber 70
72 base of specimen chamber 70
73 top opening of specimen chamber 70
80 containment system
81 bag of containment system 80
82 handle of containment system 80
83 porous structural cartridge of containment system 80
84 sample receptacle of containment system 80
85 cartridge base of containment system 80
86 sample receptacle apertures of containment system 80
87 cartridge cover of containment system 80
88 additional cartridge base of containment system 80
90 inner plug
91 handle of inner plug 90
100 self-venting cap
101 lower component of self-venting cap 100
102 upper component of self-venting cap 100
102a lower surface of upper component 102
103 seal of self-venting cap 100
104 third component of self-venting cap 100
105 plate
106 screw (threads not shown)
107 cover plate
108 female thread in lower component 101
111 male thread
112 female thread
113 positioning device
114 second positioning device
115 rib
121 first plurality of apertures in lower component 101
122 second plurality of apertures in upper component 102
131 first chamber of self-venting cap 100
132 second chamber of self-venting cap 100
133 vent opening of self-venting cap 100

Figure 2:
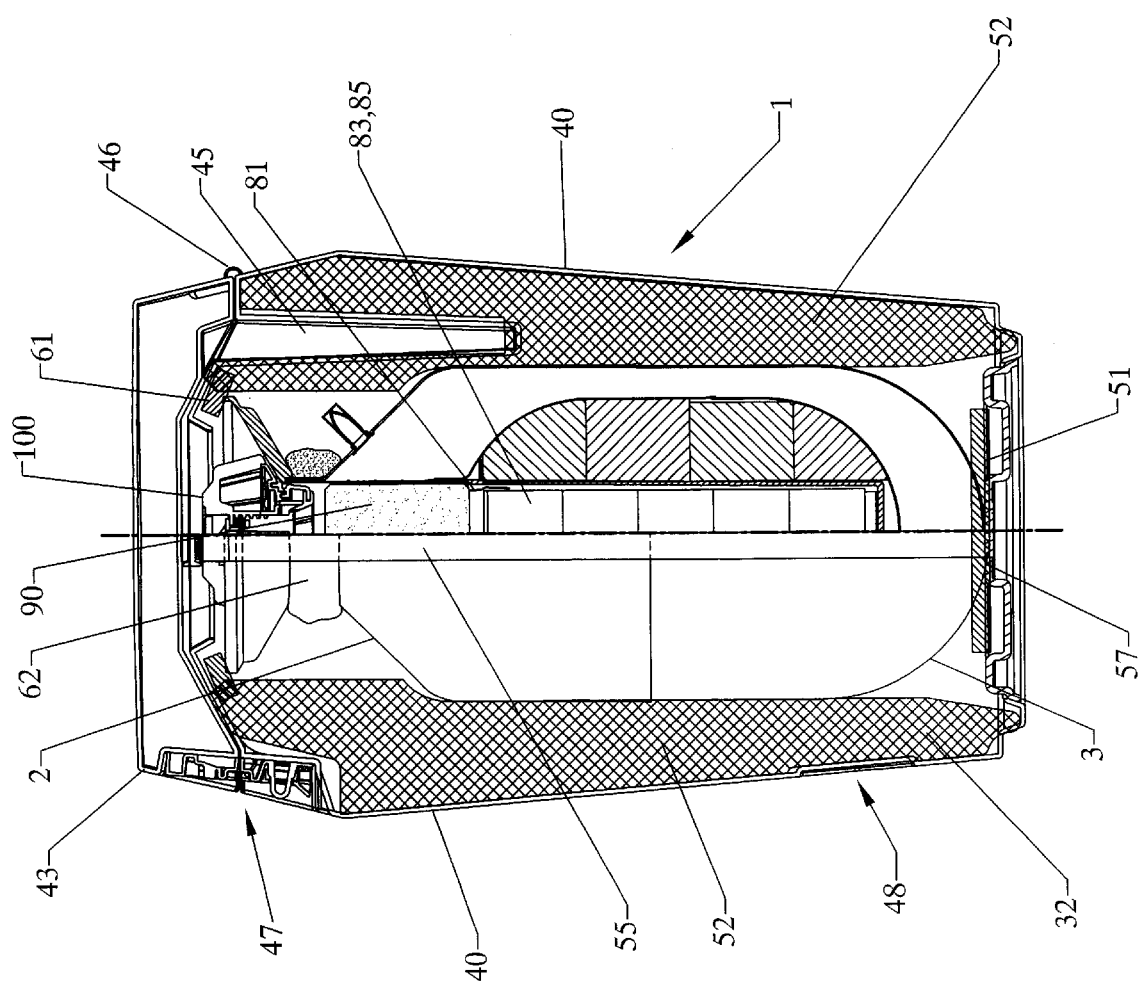
FIG. 2 is a planar cross section with a partial cutaway view of a preferred embodiment of a portable, insulated shipping container.
Figure 3:
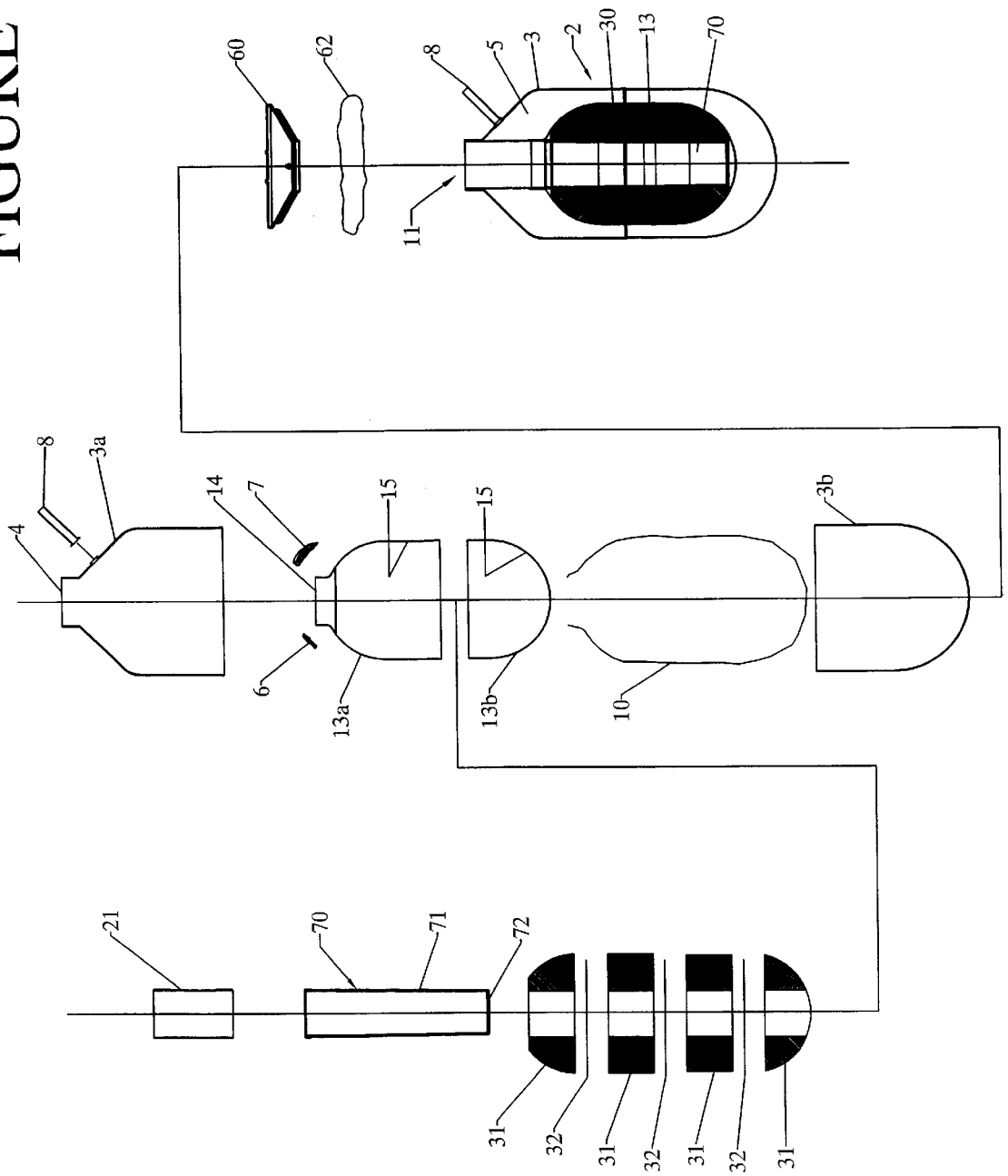
FIG. 3 is an assembly drawing of a preferred embodiment of a dewar vessel assembly.
Figure 4:
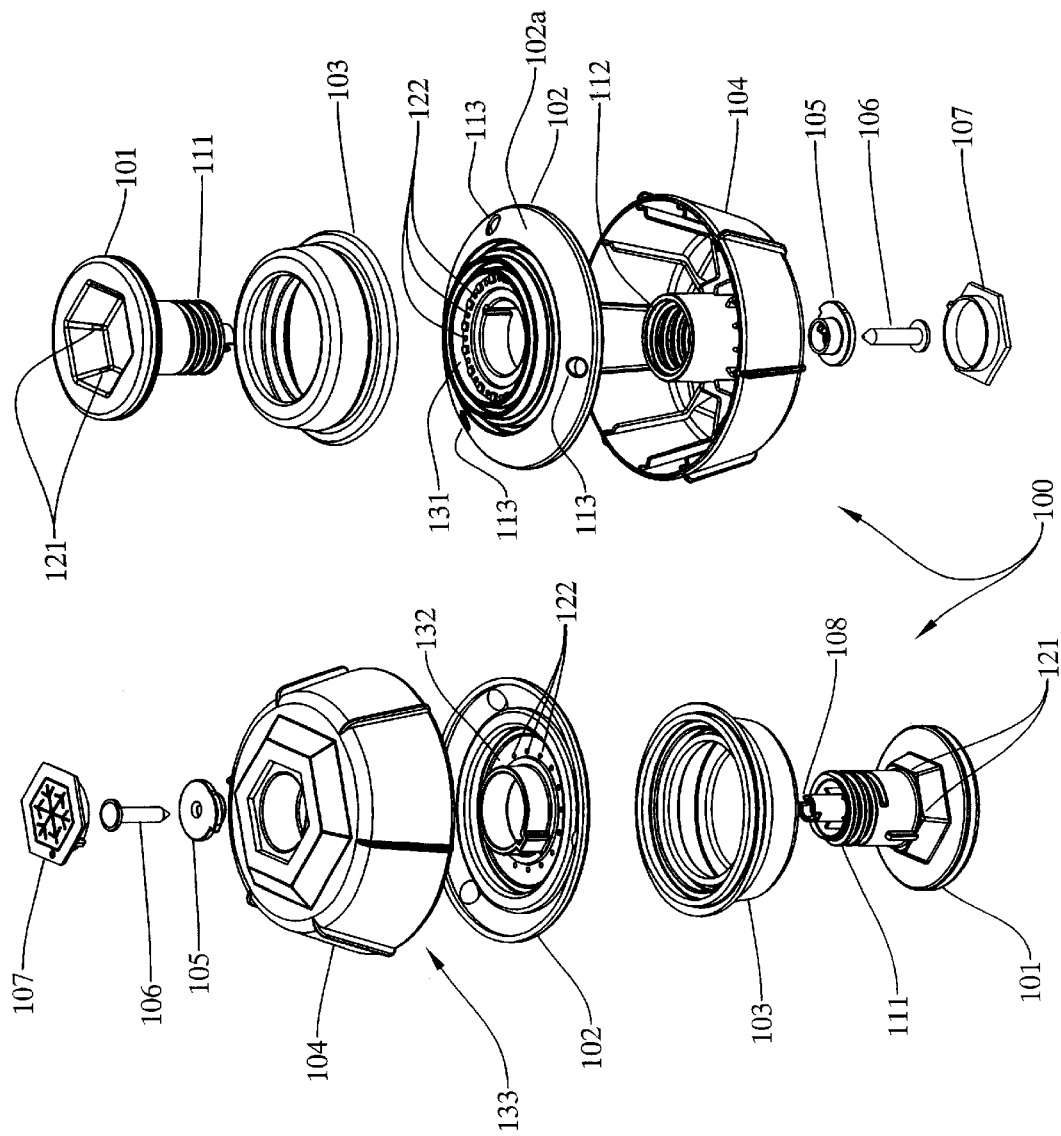
FIG. 4 is an exploded assembly drawings of a preferred embodiment of a self-venting cap taken from reverse directions.

FIG. 1 provides an assembly drawing that illustrates all of the components of the cryogenic shipping container, generally designated as 1, in a disassembled state, and FIG. 2 illustrates how all of these components fit together in assembled state. FIG. 3 is an assembly drawing that illustrates how dewar vessel 2 is assembled.

Figure 5B:
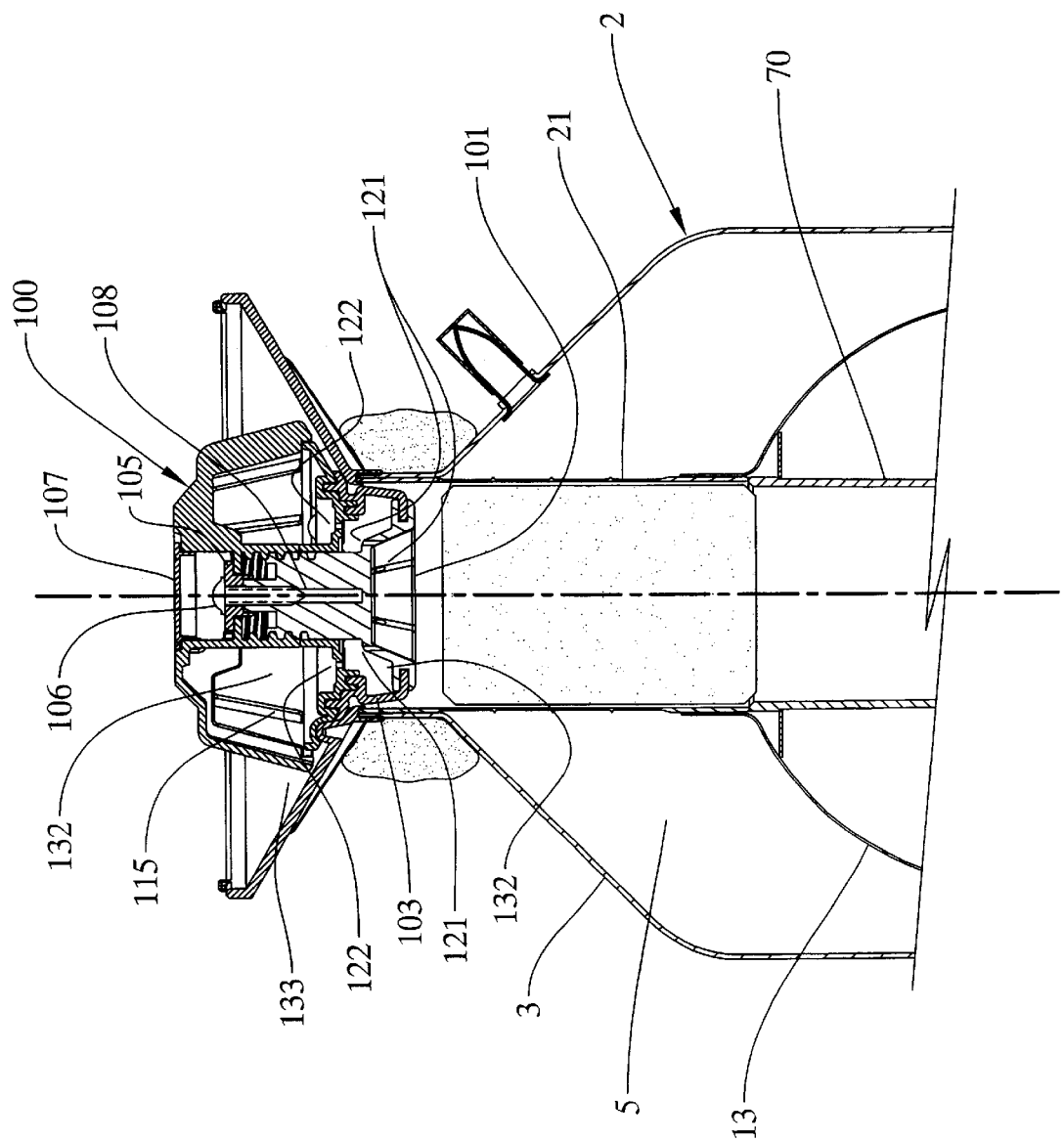

As shown in FIG. 1, the dewar vessel, generally designated as 2, has a specimen chamber 70 that is accessed by a dewar opening 11. When shipping container is ready for use after it has been fully charged with a liquid cryogen, a sample receptacle is placed inside of specimen chamber 70 through dewar opening 11. As shown in FIG. 1, and as described in greater detail in connection with FIG. 6, one form that the sample receptacle may take is a containment system 80 in which a porous structural cartridge 83 is held within a bag 81 with a handle 82. After containment system 80 is placed inside of specimen chamber 70, an inner plug 90, with a handle 91, is placed inside of dewar opening 11. (Inner plug 90, which can be made of polyurethane foam that is cryogenically compatible, acts as both a spacer and an insulator.) Next, a self-venting cap 100 is inserted into dewar opening 11 through funnel-shaped vessel plate 60 and tightened so as to create a compression seal (this is shown in FIGS. 5A–5C). After the compression seal has been formed, an adjustable buckle 56 of safety strap 55 can be closed and tightened (any suitable alternative connection mechanism could be substituted for a buckle, if desired). Safety strap 55 can be made of a webbing material, and it is affixed to an outer bottom 57 of dewar vessel 2 by adhesive tape or some other affixation means. Safety strap 55, when properly closed and tightened, provides additional integrity to dewar vessel 2 and helps prevent loss or separation of self-venting cap 100 and containment system 80.

The dewar vessel assembly is held within an outer shipping container shell 40 made of a lightweight, but rigid, material that helps to provide shock and impact resistance, such as low density polyethylene. Outer shipping container shell 40 has a "base" 41, a "side wall" 42, and a "top wall" 43 that surround and enclose dewar vessel 2 during shipping. From a definitional standpoint, when container 2 is resting upon a flat planar surface (such as the ground or a floor of a transportation vehicle) in its intended and desired orientation (in other words, not on its side or upside down), base 41 is the portion of shell 40 that rests upon the flat planar surface, top wall 43 is the outermost portion of shell 40 distant from base 41 which is somehow movable to permit access inside of the container (e.g., the top lid of a box) and side wall 42 is whatever connects base 41 to top wall 43 (e.g., a square box or rectangle has four planar surfaces that form the side wall).

Dewar vessel 2 can be inserted into shell 40 through base 41 and then base 41 can be affixed to side wall 42 by a suitable sealing means, such as screws. Mechanisms for providing evidence of tampering with shell 40, or improper orientation of container 1 during shipping, or means for tracking container 1 during shipping (e.g., by a global positioning system), can be enclosed within shell 40 at or near base 41. In the preferred embodiment of shipping container 1 illustrated in FIG. 1, top wall 43 is a cover that is attached to side wall 42 by a hinge mechanism 46 (comprised of two hinges) and a latch mechanism 47. During shipping, latch mechanism 47 can be held in a locked position by a lock (not shown) to provide security against tampering. (In this context, a "lock" could include not only a traditional lock that might require a key or combination to open, but also a secured band or tamperproof device or a device that would indicate that tampering has occurred.) Top wall 43, in a closed position, covers a top side wall 42a of side wall 42. Top side wall 42a includes a top opening 42b through which dewar opening 11 can be accessed when top wall 43 is in an open position, latch mechanism 47 is undone, and self-venting cap 100 is removed. Top side wall 42a also includes a pocket 45 for paperwork (e.g., an inventory check list, shipping documents or operating instructions). Pocket 45 is accessible when top wall 43 is not latched in place to side wall 42 and inaccessible when it is latched in place. Handles 44 can be molded into side wall 42. Side wall 42 can also have a certification plate assembly 48 (a certification plate 48a held in indentation 48c by rivets 48b) for affixing and displaying important information, such as a container serial number, certifications, warnings, bar codes, etc.

A support assembly 50 holds dewar vessel 2 within shell 40. In an especially preferred embodiment, support assembly 50 is made up of several different pieces of lightweight, shock-absorbing foam material. Support assembly 50 has a bottom portion 51 in contact with base 41 to protect the bottom of dewar vessel 2, side rib portions 52 in contact with side wall 42 to protect the sides of dewar vessel 2, and a top portion 53 to protect the top of dewar vessel 2. Side rib portions 52 can be attached to side wall 42 by adhesive or tape. Top portion 53 of support assembly 50 can be held in place by rib portions 52.

As shown in FIG. 1, shipping container 1 includes a funnel-shaped vessel plate 60. The funnel shape of plate 60 makes it easier to pour liquid cryogen into dewar vessel 2. It also helps to restrict access into the interior of shell 40 through top opening 42b. It also contains a position device 114 which are three nubs that are used by self-venting cap 100 to help lock it in place and form a compression seal with the outer circumference of neck portion 21 of dewar vessel 2. (Throughout this description, and in the attached claims, "circumference" or "circumferential" is used to refer to a perimeter or periphery, which may or may not be circular. Thus, by way of example, the inner circumference of a square neck would have a square shape.) Vessel plate 60 is held in place by sealing it to neck portion 21 by adhesive so that there is no liquid or vapor gap between vessel plate 60 and neck portion 21. Additional stability for the seal is provided by spray foam 61, and supports 61 help position and support plate 60 inside of shell 40. Vessel plate 60 should be made of a cryogenically compatible material.

Once shipping container 1 is fully assembled, dewar vessel 2 should be held securely within shell 40 in a fixed position, and shell 40 and support 50 should provide impact resistance and protection to dewar vessel 2 in any spatial orientation. When it is in its normal, upright position, i.e., when its weight is resting on base 41, specimen chamber 71 is substantially perpendicular to base 41. This is the optimal position for container 1 because of the physical characteristics of vaporous cryogen, such as nitrogen. Vapor phase liquid nitrogen has a greater density than air, so it will behave similar to a liquid when it is confined within a container. As long as the vapor phase liquid nitrogen is retained within the dewar vessel, it helps to maintain cryogenic temperatures in the dewar vessel necessary for the cryopreservation of biologicals. This is because the temperature of vapor phase liquid nitrogen is cryogenic (100K). However, if the dewar vessel is positioned upside down, the vapor phase liquid nitrogen will egress from the dewar vessel, much like a fluid, because vapor phase liquid nitrogen in denser than air. Thus, when the dewar vessel is positioned upright, the vapor phase liquid nitrogen will accumulate in the dewar vessel until sufficient pressure buildup forces excess vapor phase liquid nitrogen out of the dewar vessel.

Although it is highly desirable for shipping container 1 to be stored and shipped in its upright position when it is charged with a liquid cryogen, the realities associated with modern day shipping do not always assure such a result. The preferred embodiment of a shipping container shown in FIG. 1 seeks to address this reality, and increase its efficiency, in a simple and economical fashion. Outer shell 40 is designed so that if container 1 ends up being stored or shipped on its side, specimen chamber 70 and dewar opening 11 will still be held at an angle thereby creating a reservoir. The reservoir will have the effect of retaining vapor phase liquid cryogen. By contrast, if no reservoir exists, specimen chamber 70 and dewar opening 11 would be positioned in a substantially parallel position relative to the ground. Such parallel positioning would result in the vapor phase liquid nitrogen pouring out of the vessel in a similar fashion to a glass of water tipping over and spilling its contents.

To create a reservoir, side wall 42 is designed so that when it rests on a flat planar surface the angle formed by the intersection of the planar cross section of specimen chamber 70 with the flat planar surface is approximately six degrees or greater. This is accomplished for container 1 shown in FIG. 1 by making the six planar portions of side wall 41 progressively wider as they extend away from base 41 until they reach a maximum thickness near top wall 43. The exact degree of the angle is a matter of design choice, and it will depend upon the overall configuration of the container and the desired result. However, the angle should be sufficient to produce a functional reservoir. In addition, using a self-venting cap 100 that forms a compression seal about the inner circumference of neck 21 will increase the volume of the reservoir.

The basic design and functioning of a "dewar vessel" is well known and long established. In fact, the term "dewar vessel" is defined in *Webster's third new international dictionary of the English language, unabridged* (1981) as "a usu. glass or metal container with at least two walls that has the space between the walls evacuated so as to prevent the transfer of heat, often has a coating (as silvering) on the inside to reduce radiation, and is used esp. for storing liquefied gases (as liquid air) or for investigations at low temperatures." Examples of various United States Patents that teach the use of dewar vessels with a liquid cryogen for use in a shipping container include U.S. Pat. Nos. 2,396,459, 3,298,185, 4,481,779 and 4,495,775. The dewar vessels disclosed in these patents, and dewar vessels used in shipping containers today, share certain common characteristics. These characteristics, which will hereinafter be defined as being present in a dewar vessel, are an outer casing and an inner vessel with each having openings at their tops connected together by a neck portion forming an evacuable space between the outer casing and the inner vessel and a dewar opening into the inner vessel.

A preferred embodiment of dewar vessel 2 according to the present invention is constructed as follows. Neck portion 21 is sealed to specimen chamber 70 by epoxy. A plastic foam 30 that holds a liquid cryogen (not shown) is formed in several segments 31 that are separated by a capillarity separation layer 32. Plastic foam 30 surrounds specimen chamber 70, and then this assembly is placed inside of upper half 13a and lower half 13b which are joined together to form inner vessel 13 with an opening 14 at its top. A getter pack 6 and a desiccant 7 are secured to the top outside of inner vessel 13 by epoxy and metal tape, respectively. (The use of a getter pack and a desiccant are well known within the industry and are not an inventive aspect of the present invention.) Next, a layer of super insulation 10 is used to surround this assembly. For ease of manufacture and economy, it is especially preferred that super insulation 10 be spirally wrapped and that it be constructed of a single component (e.g., a one-sided metalized polymer film), The top of neck portion 21 is then sealed to an opening 4 in upper half 3a by epoxy which is joined together with lower half 3b to form outer casing 3 and an evacuable space 5 between outer casing 3 and inner vessel 13. Once dewar vessel 2 is assembled, evacuable space 5 can only be accessed through nipple 8, specimen chamber 70 can only be accessed through dewar opening 11, and cryogen cannot pass between specimen chamber 70 and plastic foam 30 (whether in a liquid or in a gaseous state) except through side wall 71 and base 72 of specimen chamber 70. Details regarding especially preferred materials useful for constructing a dewar vessel are disclosed in U.S. Pat. No. 6,119,465.

Plastic foam 30 is preferably an open-celled plastic foam that is cryogenically compatible. It is especially preferred that plastic foam 30 be a phenolic foam (such material is inexpensive and commonly used as a water-holding base for floral arrangements). Plastic foam 30 can either be foamed in place or it can be pre-manufactured in blocks and then sectioned down into segments and inserted into the space surrounding specimen chamber 70. It is especially preferred that plastic foam 30 occupies substantially all of the volume between inner wall 15 of inner vessel 13 and specimen chamber 70.

The open cell structure of plastic foam 30 retains a liquid cryogen, such as liquid nitrogen, by absorption, adsorption, and surface tension as it saturates foam 30. The physical properties of a liquid cryogen (such as liquid nitrogen) and plastic foam 30 are such that the liquid cryogen remains in plastic foam 30 and does not migrate back into specimen chamber 70 when plastic foam 30 is properly charged and comprised of correctly dimensioned segments 31. Plastic foam 30 can absorb liquid nitrogen up to six times faster than previously used materials. This feature accelerates the process of charging dewar vessel 2 with liquid cryogen. It is especially preferred that plastic foam 30 has a free volume of between approximately 85% to approximately 95%. Plastic foam 30 is preferably an "azotophilic" adsorbent capable of acquiring and retaining liquid nitrogen cryogen in place because of high surface tension that exists between the liquid nitrogen (or, if applicable, and alternative liquid cryogen) and the foam. ("Azotophilic" means nitrogen loving, i.e., having an affinity for nitrogen in any of its valence states.) As a result, shipping container 1 of the present invention can be shipped in any orientation, including upside down, without danger of spilling or having the liquid nitrogen directly contact a specimen vial.

It is especially preferred that multiple segments 31 of plastic foam 30 have a thickness or height, measured in any dimension, for a given type of foam material and cryogen, such that the liquid cryogen held within the chosen foam will not ooze or flow out of the foam when the orientation of the foam is changed. In other words, at least one linear dimension of a segment will be exceeded if the segment is capable of holding liquid cryogen in one spatial orientation but oozes cryogen in any other orientation. It is also especially preferred that the linear dimensions of foam segments 31 be chosen to optimize the amount of liquid cryogen held within plastic foam 30 (i.e., all of foam segments 31 combined) while minimizing the number of capillarity separation layers 32 required to separate foam segments 31.

It is believed that the preferred embodiment of plastic foam is superior because it possesses a micro-porous structure that promotes capillarity, or capillary action. Capillary action is the result of adhesion (adsorption) and surface tension. Adhesion of a liquid to the walls of a uniform circular vessel (or tube or pore) will cause an upward force on the liquid at the edges of the vessel. Surface tension acts to hold the surface intact, so instead of just the edges moving upward, the whole liquid surface is dragged upward. Capillary action occurs when the adhesion of the liquid to the walls is stronger than the cohesive forces between the liquid molecules. The height to which capillary action will take a liquid in a uniform circular tube is limited by surface tension. The height to which capillary action will lift a fluid depends on the weight of the fluid. At some point the force of capillary action in one direction is counteracted by the force of gravity (weight of the fluid) in an opposite direction and the suspended fluid falls because of its own weight. For a cylindrical capillary tube, this height can be determined from the formula $h=2T/prg$ where h equals the maximum height, T equals surface tension of the liquid, p equals density of the liquid (i.e., mass/volume), r equals the radius of the capillary tube, and "g" is needed to change mass (density in grams) to force.

It is not necessary that the plastic foam of the present invention is made up of perfect capillary tubes (i.e., cylindrical tubes) or that the maximum height of the segments of plastic foam used in the present invention be determined by the formula stated above; instead, the important characteristic is that the plastic foam exhibits strong capillary action. Capillary action is limited by a maximum dimensional height, which will hereinafter be defined as a "critical height," that a given liquid cryogen will reach in the capillary like pores of the adsorbent plastic foam in a given spatial orientation. When the plastic foam exceeds this height, any additional plastic foam exceeding the critical height is physically incapable of retaining additional liquid cryogen in-situ as a result of capillary action. When plastic foam is physically incapable of retaining liquid cryogen by capillary action, it fails to maximize the amount of liquid cryogen retained within the volumetric space it occupies. Thus, it is desirable that the height of a given segment of plastic foam is equal to, or less than, its critical height for its intended liquid cryogen (which is usually liquid nitrogen). The same principle is applicable to other dimensions if the plastic foam is being held within a container in which it could have other orientations that would cause the height of plastic foam in a given orientation to exceed the critical height.

Capillarity separation layers 32 do not have to be especially thick. Instead, their thickness is dependent upon a thickness that is required to perform their intended function for a given plastic foam and an intended liquid cryogen. Capillarity separation layers 32 function to seal off a plastic foam so as to limit the functional height of its capillary like pores, and thereby permit segments of plastic foam to have a height less than the critical height, and thereby prevent liquid cryogen from oozing or flowing out of the segments if their spatial orientation is changed. Capillarity separation layers 32 should be made of a cryogenically compatible material, such as treated paper, Tyvek® spunbonded olefin, or Teflon® FEP. A 3 mm layer of Tyvek® has been found to perform this function well. Empirical results indicate that approximately four inches is a suitable, maximum critical height for the type of plastic foam described herein, and it is especially preferred that multiple segments 31 have a thickness of greater than approximately three inches, with a thickness of about 3.5 inches being especially preferred.

It is especially preferred that specimen chamber 70 be made of an open-celled porous thermoplastic material that is cryogenically compatible, such as an aerated polypropylene foam. Specimen chamber 70 can be formed in a single piece construction with a base 72 connected to a cylindrically-shaped side wall 71 having a top opening 73. The outer circumference of side wall 71 at top opening 73 is sealed to either neck portion 21 or an inner wall of inner vessel 13. Specimen chamber 70 should allow liquid cryogen to pass through it into plastic foam 30 and allow the cryogen in a vaporous state to pass into it from absorbent foam 30. The thermoplastic material of specimen chamber 70 acts as a filter to prevent particles or fragments of plastic foam 30 from entering into specimen chamber 70, and it also acts as a wicking device for rapid transfer of the liquid cryogen into plastic foam 30. In addition to its superior physical properties, specimen chamber 70 is lightweight and less expensive to manufacture than previous specimen chambers made of metal or a metal alloy.

The combination of specimen chamber 70 and plastic foam 30 in the preferred embodiment of dewar vessel 2 results in more efficient utilization of the volume of inner vessel 13 with greatly reduced charging time. Unlike many prior dewar vessels, plastic foam 30 occupies substantially all of the volume between inner wall 15 of inner vessel 13 and sample chamber 70, and liquid cryogen can rapidly pass from specimen chamber 70 into plastic foam 30 along the entire length of side wall 71. The decreased time required to fully charge a dewar vessel with liquid cryogen is attributable to the physical properties of specimen chamber 70 and plastic foam 30. These properties can be demonstrated by pouring up to approximately fifty percent of a full charge of liquid cryogen into specimen chamber 70 of shipping container 1 and then turning container 1 upside down. By the time shipping container 1 is turned upside down, all of the liquid cryogen will be retained by plastic foam 30 and virtually no liquid cryogen will be released.

FIGS. 4A and 4B illustrate an especially preferred self-venting cap 100 for use with a dewar vessel 2. The manner in which such a cap functions in an especially preferred application of shipping container 1 is illustrated in FIGS. 5A–5C. Self-venting cap 100 has four primary components—a lower component 101 with a first plurality of apertures 121, an upper component 102 with a second plurality of apertures 122, a seal 103, and a third component 104. It is especially preferred that all of these four primary components be constructed of a cryogenically compatible material that is non-metallic and non-conductive. The first, second and fourth components can be made of an injection moldable material such as Acetyl. The outer circumference of lower component 101 is less than the inner circumference of neck 21 and the first plurality of apertures 121 is located inside of the outer circumference of the lower component as shown in FIGS. 4A and 4B.

When self-venting cap 100 is assembled, seal 103, which is preferably made of silicone rubber, is attached to lower component 101 by a snap, friction fit. Lower component 101 is secured to upper component 102 and third component 104 by two different means.

First, a screw 106 (threads not shown) is screwed into a female thread 108 in lower compartment 101 and held in place by plate 105. A cover plate 107 (shown with a trademark of Cryoport, Inc.) covers and seals the chamber in third component 104 in which the top of plate 105 and the head of screw 106 are held. Screw 106 holds all four primary components together in a cap assembly in which the individual primary parts can still move relative to each other. In this assembly, second component 102 is held between first component 101 and third component 104, and seal 103 is held between first component 101 and second component 102.

Second, lower component 101 has a male thread 111 that screws into female thread 112 of third component 103. When male thread 111 is not fully screwed into female thread 112, seal 103 is held in a taut position (see FIG. 5B) relative to the position it is held when male thread 111 is fully screwed into female thread 112 in a compression seal position (see FIG. 5C). Seal 103 changes position between FIGS. 5B and 5C when third component 104, which functions as a crank top, is rotated in a tightening direction that causes seal 103 to be squeezed between lower and upper components 101 and 102 so as to form a compression seal with neck 21. (FIG. 5B shows cap 100 before it is in a compression seal position while FIG. 5C shows cap 100 once it is in a compression seal position.) Ribs 115 of third component 104 rest against upper component 102, which serve as a stop, and thereby create a plurality of vent openings, in the compression seal position. (The left half of FIG. 5C has been slightly rotated to show a clear vapor path instead of such a top.) A positioning device 113 (shown as indentations in FIG. 4B) on lower surface 102a of upper component 102 engages with a second positioning device 114 (shown as nubs in FIG. 1) to prevent cap 100 from spinning during the tightening process.

When self-venting cap 100 forms a compression seal with neck 21 of dewar vessel 2 (as shown in FIG. 5C), vapor flow between inner vessel 13 and outside of dewar vessel 2 must flow through vent opening 133. FIG. 5C illustrates one such vapor path. The path includes flow through a first chamber 131 located between lower and upper components 101 and 102, and a second chamber 132 located between second component 102 and third component 104. Vent opening 133 can be a single opening or a plurality of openings. In FIG. 5C, vent opening 133 is located between third component 104 and plate 60, but it could also be located between third component 104 and neck 21 if plate 60 is not used. Vent opening 133 is located outside of the inner circumference of neck 21 because upper component 102 has an upper outer circumference that is located outside of the inner circumference of neck 21.

Self-venting cap 100 provides many advantages over traditional caps for dewar vessels.

One advantage of self-venting cap 100 is the strength of the compression seal it forms with neck 21 of dewar vessel 2. The seal can be strong enough to support the weight of dewar vessel 2 when it is not charged with a cryogen, or even stronger. This degree of strength is important when container 1 is subjected to shock or impact because cap 100 restricts access to, and effectively seals off access to, the contents of specimen chamber 70 and specimen containment systems inside of dewar vessel 2.

Another advantage of self-venting cap 100 is that it creates a plurality of tortuous vapor paths for venting dewar vessel 2. A tortuous vapor path increases the thermal length that gas venting from the dewar vessel must travel. Increasing the thermal length increases the thermal efficiency of the dewar vessel, thereby increasing the hold time for the shipping container. Multiple venting paths increases safety because it eliminates the possibility that a single venting path might become clogged, leading to dangerous build-up of gas.

In the preferred embodiment of cap 100, each of the first plurality of apertures 121 leads into first chamber 131, and each of the second plurality of apertures 122 leads out of first chamber 131 and into second chamber 132. Thus, vapor inside of dewar vessel 2 can travel in a plurality of tortuous paths when cap 100 is in the compression seal position. The plurality of tortuous paths begin within neck 21 and then sequentially travel up through first plurality of apertures 121, first chamber 131, second plurality of apertures 132, second chamber 132 and then out vent opening 133. In addition, because of the volume of chambers 131 and 132, gas need not always leave the chamber at the same point or points. This means there are also a plurality of shorter tortuous paths beginning within the first plurality of apertures 121, travelling through first chamber 131, and then up through second plurality of apertures 122.

Because first and second chambers 131 and 132 provide a void space that can be accessed by a plurality of apertures, they create a number of different vapor paths, as already noted. However, they also provide a void space in which gas can accumulate and intermix. This creates an additional benefit because the chambers can have different temperature gradients, and gases entering or leaving these chambers can have different temperature gradients as a result of mixing with gas contained in these chambers. Chambers 131 and 132 also act as buffer zones between gas flowing from outside of cap 100 into inner vessel 13 and gas flowing from inside of inner vessel 13 to outside of cap 100.

Cap 100 can also include one or more semi-permeable membranes (not shown in the Figures) to prevent moisture (water vapor) from entering from entering into the dewar vessel while still allowing vaporous cryogen to exit from the dewar vessel. For example, such a membrane could be used to cover either or both of the first and second plurality of apertures 121 and 122. (Alternatively, or in addition, a semi-permeable membrane could be placed at any other convenient location in the vapor path shown in FIG. 5C; however, it is preferable that it be conveniently included as part of cap 100 or inner cap 90. Including a semi-permeable membrane in the cap minimizes the portion of the vapor path that is restricted by the membrane and provides the membrane with a convenient structural component for incorporation and structural integrity.)

FIG. 6 illustrates a containment system that is especially useful for dangerous materials (such as potentially biohazardous or infectious agents) that is designed and constructed to withstand the standards of UN Class 6.2 certification. When this containment system is used with self-venting cap 100 illustrated in FIGS. 4A and 4B in an especially preferred shipping container as illustrated in FIGS. 1 and 2, the result is an economical and superior shipping container that meets rigid shipping regulations concerning shipment of dangerous (infective) materials.

Containment system 80 is based upon a primary porous structural cartridge 83 and a bag 81. As shown in steps 1 through 4 of FIG. 4, structural cartridge 83 is placed into bag 81, bag 81 is sealed to complete containment system 80, and then containment system 80 can be lowered into specimen chamber 70 through dewar opening 11 by bag handle 82. Handle 82 can be made from a loop of the polymer film used to make bag 81.

Bag 81 is made of a cryogenically compatible polymer film with a sealing mechanism that assures a liquid and vapor tight seal when actuated. A fluorinated ethylene propylene resin or a polyimide film have been found suitable for this purpose, and Teflon® FEP Grade 160 or Kapton® FN film are especially preferred. Teflon® FEP is a fluorinated ethylene propylene resin that meets American Society for Testing and Materials ("ASTM") Standard Specification D2116-97 for FEP-Fluorocarbon Molding and Extrusion Materials. Kapton® FN is a high-quality plastic film commercially available from DuPont. It is believed that Tyvek® spunbonded olefin, and in particular DuPont® Medical grade Tyvek® types S-1059-B and S-1073B, are also suitable for use as bag 81. The sealing mechanism should create a seal that prevents liquid or vapor from entering or leaving the interior of bag 81. The sealing mechanism can be a mechanical closure (in which case it is especially preferred that it be constructed of two materials with dissimilar coefficients of thermal expansion), an adhesive joint, or a heat seal.

It is especially preferred that structural cartridge 83 contain more than one cartridge. Each cartridge has a plurality of sample apertures to hold a plurality of sample receptacles separate from one another. The top cartridge of structural cartridge 83 has a base 85 and a cover 87 that mates with cartridge base 85 to enclose the plurality of sample receptacle apertures 86 and any sample receptacles 84 (vials) held within said plurality of sample receptacle apertures. The bottom of cartridge base 85 is designed so that it can function as a cover 87 to mate with an additional cartridge base 88. Stacking additional cartridge bases in the same fashion increases the size of cartridge 83. The components of structural cartridge 83 (i.e., cover 87, base 85 and any additional bases 88) are made of a polypropylene polymer compound. Each cartridge has sufficient absorbing capacity to absorb the entire contents of all of the plurality of sample receptacles held within the plurality of sample receptacle apertures. It is especially preferred that each cartridge have sufficient absorbing capacity to absorb twice the entire contents of all of the plurality of sample receptacles held within the plurality of sample receptacle apertures.

Structural cartridge 83 performs two essential requirements of the Dangerous Goods Regulations. The first requirement, separation of the primary receptacles, is required by IATA Packing Instruction 602 which states "[m]ultiple primary receptacles placed in a single secondary packaging must be wrapped individually or for infectious substances transported in liquid nitrogen, separated and supported to ensure that contact between them is prevented." Cartridge 83 clearly meets this requirement and is an advance over current practices in the art in which it is common just to wrap receptacles loosely in sheets of absorbent cloth. The second requirement, found in IATA 602, states "[t]he absorbing material, for example cotton wool, must be sufficient to absorb the entire contents of all primary receptacles." Again, cartridge 83 does this, with additional safety, and represents a significant advance in the current state of the art.

Although the foregoing detailed description is illustrative of preferred embodiments of the present invention, it is to be understood that additional embodiments thereof will be obvious to those skilled in the art. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A portable, insulated shipping container, comprising:
   a dewar vessel having an outer casing and an inner vessel with each having openings at their tops connected together by a neck portion forming an evacuable space between the outer casing and the inner vessel and a dewar opening into the inner vessel;
   a specimen chamber held within the inner vessel that is accessed through the dewar opening;
   a plastic foam held within the inner vessel between an inner wall of the inner vessel and the specimen chamber;
   a self-venting cap that restricts access to the specimen chamber when it is in an engaged position;
   an outer shipping container shell having a base, a side wall attached to and extending upwardly from the base, and a top wall attached to the side wall opposite of the base, the top wall having a movable access assembly for gaining access from outside of the shipping container shell to the specimen chamber when the self-venting cap is not in an engaged position and the movable access assembly is in an open position but denying access to the self-venting cap in the engaged position when the movable access assembly is an a closed position; and
   a support assembly for holding the dewar vessel within the outer shipping container shell and providing impact and vibration resistance to the dewar vessel;
   wherein the specimen chamber allows a liquid cryogen to pass through the specimen chamber into the plastic foam and allows the liquid cryogen in a vapor phase liquid state to pass from the plastic foam into the specimen chamber;
   wherein the shipping container is configured such that when the base rests on a flat planar surface in an upright position the specimen chamber is held such that a planar cross section of the specimen chamber taken from an upper end closest to the top wall and extending down through a lower end closest to the base and continuing to the flat planar surface is substantially perpendicular relative to the flat planar surface but when the side wall rests on the flat planar surface the angle formed by the intersection of the planar cross section with the flat planar surface is approximately six degrees or greater.

2. A portable, insulated shipping container as recited in claim 1, wherein the specimen chamber has a chamber wall comprised of an open-celled porous thermoplastic material that is cryogenically compatible.

3. A portable, insulated shipping container as recited in claim 1, wherein the chamber wall acts as a filter to prevent particles or fragments of the plastic foam from entering into the specimen chamber.

4. A portable, insulated shipping container as recited in claim 1, wherein the chamber wall is comprised of an aerated polypropylene foam.

5. A portable, insulated shipping container as recited in claim 1, wherein the plastic foam is an open cell plastic foam.

6. A portable, insulated shipping container as recited in claim 1, wherein the plastic foam is a phenolic foam.

7. A portable, insulated shipping container as recited in claim 1, wherein the plastic foam is comprised of at least two foam segments separated by a capillarity separation layer.

8. A portable, insulated shipping container as recited in claim 7, wherein the thickness of each of the foam segments is less than a critical height for use with an intended liquid cryogen.

9. A portable, insulated shipping container as recited in claim 7, wherein the thickness of the foam segments is greater than approximately three inches but less than approximately four inches.

10. A portable, insulated shipping container as recited in claim 7, wherein the capillarity separation layer is cryogenically compatible.

11. A portable, insulated shipping container as recited in claim 1, wherein the plastic foam is comprised of a plurality of foam segments and each foam segment is separated from another foam segment by a capillarity separation layer, wherein each foam segment has a thickness less than a critical height when the container is resting in an upright position.

12. A portable, insulated shipping container as recited in claim 11, wherein the foam thickness is greater than approximately three inches and less than approximately four inches.

13. A portable, insulated shipping container as recited in claim 11, wherein the thickness is selected so that the head pressure of the plurality of foam segments will not cause liquid cryogen to ooze or flow out of the foam segments when their spatial orientation is changed.

14. A portable, insulated shipping container as recited in claim 7, wherein the plastic foam occupies substantially all of the volume between the inner wall of the inner vessel and the sample chamber.

15. A portable, insulated shipping container as recited in claim 1, wherein the self-venting cap restricts access to the specimen chamber when it is in a compression seal position that forms a compression seal with an inner circumference of the neck.

16. A portable, insulated shipping container as recited in claim 15, wherein vapor inside the dewar vessel can travel in a plurality of tortuous paths when the cap is in the compression seal position, the plurality of tortuous paths beginning within the dewar opening and then sequentially traveling up through a first plurality of apertures, a first chamber, a second plurality of apertures, a second chamber and then out a vent opening.

17. A portable, insulated shipping container as recited in claim 16, wherein there is a plurality of shorter tortuous paths beginning within each of the first plurality of apertures, traveling through the first chamber, and then up through at least two of the second plurality of apertures.

18. A portable, insulated shipping container as recited in claim 1, further comprising:
a funnel-shaped vessel plate affixed to the dewar vessel and extending outwardly from the neck portion to create a liquid-tight and gas-tight funnel for the dewar opening.

19. A portable, insulated shipping container as recited in claim 18, wherein the vessel plate is comprised of a cryogenically compatible material.

20. A portable, insulated shipping container as recited in claim 19, wherein the self-venting cap restricts access to the specimen chamber when it is in a compression seal position that forms a compression seal with an inner circumference of the neck and vapor inside the dewar vessel can travel in a plurality of tortuous paths when the cap is in the compression seal position, the plurality of tortuous paths beginning within the dewar opening and then sequentially traveling up through a first plurality of apertures, a first chamber, a second plurality of apertures, a second chamber and then out a vent opening.

21. A portable, insulated shipping container as recited in claim 20, wherein the self-venting cap is comprised of:
a lower component having an outer circumference that is less than the inner circumference of the neck and the first plurality of apertures is located inside of the outer circumference;
an upper component having an upper outer circumference and the second plurality of apertures, the upper outer circumference being located outside of the inner circumference;
a seal held between the lower and upper components that forms a compression seal with an inner circumference of the neck when the lower and upper components are matingly engaged in a compression seal position; and
a third component secured to the upper component;
wherein a first chamber is formed between the lower and upper components when the lower and upper components are matingly engaged in the compression seal position; and
wherein a second chamber and a vent opening located outside of the upper outer circumference are formed between the upper and third components when the lower and upper components are matingly engaged in the compression seal position.

22. A self-venting cap as recited in claim 21, wherein the lower component, the upper component and the third component are made of cryogenically compatible material that is non-metallic and non-conductive.

23. A portable, insulated shipping container as recited in claim 21, wherein the vent opening is located between the third component and the vessel plate.

24. A portable, insulated shipping container as recited in claim 1, wherein the shipping container is comprised of a rigid thermoplastic material.

25. A portable, insulated shipping container as recited in claim 1, wherein the movable access assembly is comprised of at least one hinge mechanism and a latching mechanism.

26. A portable, insulated shipping container as recited in claim 25, wherein the latching mechanism can be held in a locked position by a lock.

27. A portable, insulated shipping container as recited in claim 18, wherein the side wall includes a top side Wall with a top opening that is smaller than an outermost circumference of the vessel plate.

28. A portable, insulated shipping container as recited in claim 27, wherein the movable access assembly is comprised of at least one hinge mechanism and a latching mechanism that can be held in a locked position by a lock.

29. A portable, insulated shipping container as recited in claim 28, wherein the top wall covers the top opening in the locked position.

30. A portable, insulated shipping container as recited in claim 29, wherein the top side wall includes a pocket for holding paperwork and the top wall covers the pocket in the locked position.

31. A portable, insulated shipping container as recited in claim 28, wherein the dewar vessel is held within the base and the side wall when the top wall is in an open position.

32. A portable, insulated shipping container as recited in claim 27, further comprising:
a safety strap with a connection mechanism that forms a closed loop when the connection mechanism is closed and an open loop when the connection mechanism is open, the safety strap being affixed to an outer bottom of the dewar vessel and orientated such that it surrounds the dewar vessel, the vessel plate and the self-venting cap when the connection mechanism is closed, the connection mechanism being accessible through the top opening when the top wall is in open position.

33. A portable, insulated shipping container as recited in claim 32, wherein the connection mechanism is an adjustable buckle that allows the safety strap to be tightened on top of the self-venting cap when it is closed.

34. A portable, insulated shipping container as recited in claim 32, wherein the support assembly is comprised of multiple shock-absorbing foam components.

35. A portable, insulated shipping container as recited in claim 32, wherein the support assembly is comprised of a unitary support that is inserted into the shipping container shell after the dewar vessel is inserted into the shipping container shell.

36. A portable, insulated shipping container as recited in claim 35, wherein the unitary support is a plastic material that is injected into the shipping container shell.

37. A portable, insulated shipping container as recited in claim 34, wherein the shipping container complies with Department of Transportation/International Air Transport Association (DOT/IATA) Dangerous Goods Regulations.

38. A portable, insulated shipping container as recited in claim 1, further comprising:
an inner plug that is held in the neck portion between the self-venting cap and a specimen container.

39. A portable, insulated shipping container as recited in claim 38, wherein the inner plug is comprised of a cryogenically compatible insulating plastic foam material with a handle.

40. A portable, insulated shipping container, comprising:
a dewar vessel having an outer casing and an inner vessel with each having openings at their tops connected together by a neck portion forming an evacuable space between the outer casing and the inner vessel and a dewar opening into the inner vessel;
a specimen chamber held within the inner vessel having a base, a side wall attached to the base, and a top opening for allowing access into the specimen chamber through the dewar opening;
a plastic foam held within the inner vessel between an inner wall of the inner vessel and the specimen chamber;

a self-venting cap that restricts access to the specimen chamber when it is in a compression seal position that forms a compression seal with an inner circumference of the neck;

an outer shipping container shell having a base, a side wall attached to and extending upwardly from the base, and a top wall attached to the side wall opposite of the base, the top wall having a movable access assembly for gaining access from outside of the shipping container shell to the specimen chamber when the self-venting cap is not in an engaged position and the movable access assembly is in an open position but denying access to the self-venting cap in the engaged position when the movable access assembly is an a closed position; and a support assembly for holding the dewar vessel within the outer shipping container shell and providing impact resistance to the dewar vessel;

wherein the specimen chamber allows a liquid cryogen to pass through the specimen chamber into the plastic foam and allows the liquid cryogen in a vapor phase liquid state to pass from the plastic foam into the specimen chamber;

wherein the self-venting cap creates a tortuous path through it when it is in the compression seal position, the tortuous path forces vapor inside the inner vessel to travel in a tortuous path beginning with a first aperture through the cap to a vent opening, and the first aperture is located in the cap inside an inner circumference of the neck;

wherein the shipping container is configured such that when the base rests on a flat planar surface in an upright position the specimen chamber is held such that a planar cross section of the specimen chamber taken from an upper end closest to the top wall and extending down through a lower end closest to the base and continuing to the flat planar surface is substantially perpendicular; and wherein the shipping container is configured such that when the side wall rests on the flat planar surface, a reservoir is formed within the dewar vessel underneath a plane that is substantially parallel to the flat planar surface which intersects with the first aperture and the base, and vapor phase liquid cryogen held within the reservoir will not be forced out of the dewar vessel by gravity.

41. A portable, insulated shipping container as recited in claim 40, wherein the specimen chamber has a chamber wall comprised of an open-celled porous thermoplastic material that is cryogenically compatible.

42. A portable, insulated shipping container as recited in claim 41, wherein the chamber wall acts as a filter to prevent particles or fragments of the plastic foam from entering into the specimen chamber.

43. A portable, insulated shipping container as recited in claim 42, wherein the chamber wall is comprised of an aerated polypropylene foam.

44. A portable, insulated shipping container as recited in claim 43, wherein the plastic foam is an open cell plastic foam.

45. A portable, insulated shipping container as recited in claim 44, wherein the plastic foam is a phenolic foam.

46. A portable, insulated shipping container as recited in claim 44, wherein the plastic foam is comprised of at least two foam segments separated by a capillarity separation layer.

47. A portable, insulated shipping container as recited in claim 46, wherein an angle formed by any line containing the first aperture, the base and the flat planar surface is approximately six degrees or greater.

48. A portable, insulated shipping container as recited in claim 47, wherein the thickness of each of the foam segments is less than a critical height for an intended liquid cryogen.

49. A portable, insulated shipping container as recited in claim 47, wherein the thickness of the foam segments is less than approximately four inches.

50. A portable, insulated shipping container as recited in claim 47, wherein the capillarity separation layer is cryogenically compatible.

51. A portable, insulated shipping container as recited in claim 40, wherein the plastic foam is comprised of a plurality of foam segments and each foam segment is separated from another foam segment by a capillarity separation layer, wherein each foam segment has a thickness less than a critical height.

52. A portable, insulated shipping container as recited in claim 51, wherein the critical height is less than approximately four inches.

53. A portable, insulated shipping container as recited in claim 51, wherein the thickness is selected so that the head pressure of the plurality of foam segments will not cause liquid cryogen to ooze or flow out of the foam segments when their spatial orientation is changed.

54. A portable, insulated shipping container as recited in claim 46, wherein the plastic foam occupies substantially all of the volume between the inner wall of the inner vessel and the sample chamber.

55. A portable, insulated shipping container as recited in claim 40, further comprising:

a funnel-shaped vessel plate made of a cryogenically compatible material affixed to the dewar vessel and extending outwardly from the neck portion to create a liquid-tight and gas-tight funnel for the dewar opening.

56. A portable, insulated shipping container as recited in claim 46, wherein the self-venting cap is comprised of:

a lower component having an outer circumference that is less than the inner circumference of the neck;

an upper component having an upper outer circumference and a plurality of apertures, the upper outer circumference being located outside of the inner circumference;

a seal held between the lower and upper components that forms the compression seal with an inner circumference of the neck when the lower and upper components are matingly engaged in a compression seal position; and a third component secured to the upper component;

wherein a first chamber is formed between the lower and upper components when the lower and upper components are matingly engaged in the compression seal position; and wherein a second chamber and a vent opening located outside of the upper outer circumference are formed between the upper and third components when the lower and upper components are matingly engaged in the compression seal position.

57. A self-venting cap as recited in claim 56, wherein the lower component, the upper component and the third component are made of cryogenically compatible material that is non-metallic and non-conductive.

58. A portable, insulated shipping container as recited in claim 57, further comprising:

a safety strap with a connection mechanism that forms a closed loop when the connection mechanism is closed and an open loop when the connection mechanism is open, the safety strap being affixed to an outer bottom of the dewar vessel and orientated such that it surrounds the dewar vessel, the vessel plate and the self-venting cap when the connection mechanism is closed, the connection mechanism being accessible through the top opening when the top wall is in open position.

59. A portable, insulated shipping container as recited in claim 57, wherein the shipping container complies with Department of Transportation/international Air Transport Association Dangerous Goods Regulations.

60. A portable, insulated shipping container as recited in claim 59, further comprising:
an inner plug comprised of a cryogenically compatible insulating plastic foam material that is held in the neck portion between the self-venting cap and a specimen container.

61. A portable, insulated shipping container, comprising:
a dewar vessel having an outer casing and an inner vessel with each having openings at their tops connected together by a neck portion forming an evacuable space between the outer casing and the inner vessel and a dewar opening into the inner vessel;
a specimen chamber held within the inner vessel having a base, a side wall attached to the base, and a top opening for allowing access into the specimen chamber through the dewar opening, the specimen chamber being comprised of an open-celled porous thermoplastic material that is cryogenically compatible;
a plastic foam held within the inner vessel between an inner wall of the inner vessel and the specimen chamber;
an outer shipping container shell; and
a support assembly for holding the dewar vessel within the outer shipping container shell and providing impact resistance to the dewar vessel;
wherein the specimen chamber allows a liquid cryogen to pass through the specimen chamber into the plastic foam, allows the liquid cryogen in a vapor phase liquid state to pass from the plastic foam into the specimen chamber, and acts as a filter to prevent particles or fragments of the plastic foam from entering into the specimen chamber; and
wherein the plastic foam holds a normal charge of liquid cryogen so that once the normal charge has passed through the specimen chamber into the plastic foam, it will not return to the specimen chamber in a liquid state in any spatial orientation of the container.

62. A portable, insulated shipping container as recited in claim 61, wherein the open-celled porous thermoplastic material is an aerated polypropylene foam.

63. A portable, insulated shipping container as recited in claim 62, wherein the plastic foam is an open cell plastic foam.

64. A portable, insulated shipping container as recited in claim 63, wherein the plastic foam is a phenolic foam.

65. A portable, insulated shipping container as recited in claim 63, wherein the plastic foam is comprised of at least two foam segments separated by a capillarity separation layer.

66. A portable, insulated shipping container as recited in claim 65, wherein the thickness of the foam segments, measured in any spatial orientation of the shipping container, is less than a critical height.

67. A portable, insulated shipping container as recited in claim 61, further comprising:
a self-venting cap that restricts access to the specimen chamber when it is in a compression seal position that forms a compression seal with an inner circumference of the neck.

68. A portable, insulated shipping container as recited in claim 67, wherein the self-venting cap creates a tortuous path through it when it is in the compression seal position, the tortuous path forces vapor inside the inner vessel to travel in a tortuous path beginning with a first aperture through the cap to a vent opening, and the first aperture is located in the cap inside an inner circumference of the neck.

69. A portable, insulated shipping container as recited in claim 68, wherein the shipping container is configured such that when a side wall of the shell rests on a flat planar surface, a reservoir is formed within the dewar vessel underneath a plane that is substantially parallel to the flat planar surface which intersects with the first aperture and the base, and vapor phase liquid cryogen held within the reservoir will not be forced out of the dewar vessel by gravity.

70. A portable, insulated shipping container as recited in claim 1, further comprising:
a semi-permeable membrane that prevents moisture from entering into the dewar vessel while still allowing vaporous cryogen to exit from the dewar vessel.

71. A portable, insulated shipping container as recited in claim 70, wherein the semi-permeable membrane is incorporated into the self-venting cap.

72. A portable, insulated shipping container as recited in claim 38, wherein the semi-permeable membrane is incorporated into the self-venting cap.

73. A portable, insulated shipping container as recited in claim 40, further comprising:
a semi-permeable membrane that prevents moisture from entering into the dewar vessel while still allowing vaporous cryogen to exit from the dewar vessel.

74. A portable, insulated shipping container as recited in claim 61, further comprising:
a semi-permeable membrane that prevents moisture from entering into the dewar vessel while still allowing vaporous cryogen to exit from the dewar vessel.

75. A dewar vessel having an outer casing and an inner vessel with each having openings at their tops connected together by a neck portion forming an evacuable space between the outer casing and the inner vessel and a dewar opening into the inner vessel, the improvement comprising:
a specimen chamber held within the inner vessel having a base, a side wall attached to the base, and a top opening for allowing access into the specimen chamber through the dewar opening, the specimen chamber being comprised of an open-celled porous thermoplastic material that is cryogenically compatible;
a plastic foam held within the inner vessel between an inner wall of the inner vessel and the specimen chamber, the plastic foam having a plurality of foam segments with a thickness less than a critical height for use with an intended liquid cryogen, each of the plurality of foam segments being separated by a capillarity separation layer;
wherein the specimen chamber allows a liquid cryogen to pass through the specimen chamber into the plastic foam, allows the liquid cryogen in a vapor phase liquid state to pass from the plastic foam into the specimen chamber, and acts as a filter to prevent particles or fragments of the plastic foam from entering into the specimen chamber; and wherein the plastic foam holds a normal charge of the intended liquid cryogen so that once the normal charge has passed through the specimen chamber into the plastic foam, it will not return to the specimen chamber in a liquid state in any spatial orientation of the container.

76. A dewar vessel as recited in claim 75, wherein the open-celled porous thermoplastic material is an aerated polypropylene foam.

77. A dewar vessel as recited in claim 75, wherein the plastic foam is an open cell plastic foam.

78. A dewar vessel as recited in claim 75, further comprising:

a self-venting cap that restricts access to the specimen chamber when it is in a compression seal position that forms a compression seal with an inner circumference of the rock.

79. A dewar vessel as recited in claim 67, wherein the self-venting cap creates a tortuous path through it when it is in the compression seal position, the tortuous path forces a vapor inside the inner vessel to travel in a tortuous path beginning with a first aperture through the cap to a vent opening, and the first aperture is located in the cap inside an inner circumference of the neck.

* * * * *